United States Patent [19]

Couche

[11] Patent Number: 4,987,902
[45] Date of Patent: Jan. 29, 1991

[54] APPARATUS FOR TRANSMITTING PATIENT PHYSIOLOGICAL SIGNALS

[75] Inventor: Charles A. Couche, Seattle, Wash.

[73] Assignee: Physio-Control Corporation, Redmond, Wash.

[21] Appl. No.: 292,496

[22] Filed: Dec. 30, 1988

[51] Int. Cl.$^5$ ............................................. A61B 5/04
[52] U.S. Cl. .................... 128/696; 324/99 D
[58] Field of Search ............... 128/908, 901, 696, 664; 324/99 D

[56] References Cited

U.S. PATENT DOCUMENTS

| | | | |
|---|---|---|---|
| 3,699,389 | 10/1972 | Holsinger . | |
| 3,742,947 | 7/1973 | Hashem | 128/696 |
| 3,794,841 | 2/1974 | Cosentino et al. . | |
| 3,808,502 | 4/1974 | Babilius | 128/908 |
| 3,808,504 | 4/1974 | Babilius | 128/908 |
| 3,905,355 | 9/1975 | Brudny . | |
| 3,915,154 | 10/1975 | Cosentino . | |
| 3,965,467 | 6/1976 | Monger | 324/99 D |
| 4,127,810 | 11/1978 | Purland | 324/99 D |
| 4,245,650 | 1/1981 | Welker et al. . | |
| 4,254,406 | 3/1981 | Meares | 324/99 D |
| 4,254,776 | 3/1981 | Tanie et al. | 128/908 |
| 4,261,369 | 4/1981 | Allor . | |
| 4,321,932 | 3/1982 | Francis . | |
| 4,453,218 | 6/1984 | Sperinde et al. . | |
| 4,679,568 | 7/1987 | Blau et al. . | |
| 4,742,831 | 5/1988 | Silvian | 128/710 |

FOREIGN PATENT DOCUMENTS 0208074  3/1984  German Democratic Rep. ..................... 128/908

Primary Examiner—Lee S. Cohen
Assistant Examiner—Kennedy J. Schaetzle
Attorney, Agent, or Firm—Christensen, O'Connor, Johnson & Kindness

[57] ABSTRACT

An apparatus (10) for transmitting a patient physiological signal is provided. A converter (12) includes a front end circuit (28) that receives and conditions a patient physiological signal, $V_P$, and produces conditioned signal, $V_C$. A magnitude of $V_C$ is proportional to an amplitude of $V_P$ offset by a negative DC voltage. A track and ramp circuit (30) receives $V_C$ and produces a tracking voltage, $V_T$. A magnitude of $V_T$ is inversely proportional to the magnitude of $V_C$ when the track and ramp circuit is in a tracking mode. A controller (16) includes a clock that produces clock pulses, $V_{CK}$ and a divider (38) that divides the clock pulse frequency and produces a trigger pulse, $V_{TRIG}$. A leading edge of the $V_{TRIG}$ pulse starts a counter (40) counting $V_{CK}$ pulses. The leading edge of an optically transmitted $V_{TRIG}$ pulse is applied to the latch circuit (32), which produces a ramp command voltage, $V_R$. A high $V_R$ voltage places the track and ramp circuit (30) in a ramping mode and causes the magnitude of $V_T$ to decay at a constant rate. The latch circuit produces an echo pulse, $V_E$, when $V_T$ decays to zero volts. An optically transmitted $V_E$ pulse is applied to the counter (40). A leading edge of the optically transmitted $V_E$ pulse stops the counter (40) from counting $V_{CK}$ pulses. The counter (40) produces an output signal, $S_{OUT}$, having a value in the form of $V_{CK}$ pulses counted by the counter (40) during the elapsed time between the production of the $V_{TRIG}$ pulse and the receipt of the optically transmitted $V_E$ pulse. The $S_{OUT}$ value is proportional to the amplitude of $V_P$.

26 Claims, 3 Drawing Sheets

APPARATUS FOR TRANSMITTING PATIENT PHYSIOLOGICAL SIGNALS

FIELD OF THE INVENTION

This invention is directed to medical equipment and, more particularly, to an apparatus for use with medical monitoring and diagnostic equipment that is connected to a patient by electrode leads.

BACKGROUND OF THE INVENTION

Today medical personnel are able to monitor and diagnose a patient's physical condition by noninvasive techniques using various types of monitoring and diagnostic equipment. For example, an attending physician may determine the cardiac activity of a patient by reviewing an electrocardiogram (ECG) produced by ECG monitoring equipment connected to the patient. Additional diagnostic equipment may further analyze the ECG signals and permit the physician to make a thorough diagnosis of the patient's cardiac system.

Medical monitoring and diagnostic equipment typically receive patient physiological signals from electrode leads that connect the medical equipment to the patient. The electrode leads usually consist of an electrode attached to the patient and an electrical conductor that connects the electrode to the medical equipment. In order to protect the patient from being inadvertently shocked by the medical equipment, the electrode leads and, thus, the patient, are isolated from ground. By isolating the patient from ground, the patient is protected from potentially harmful ground currents associated with the nonisolated medical equipment.

The electrode leads are typically isolated from ground by connecting them to the medical equipment through isolating couplers, such as inductive or optical isolating couplers. Both inductive and optical isolating couplers are well known in the prior art and both present problems that are solved by the apparatus of the present invention. Basically, an inductive coupler is a transformer. One winding of the transformer is connected to the patient lead and the other winding is connected to the medical equipment. The mutual inductance between the transformer windings permits the patient physiological signals to be inductively (i.e., magnetically) coupled to the medical equipment. These inductive couplers are normally housed in the medical equipment. Unfortunately, the inductive couplers are large and bulky in comparison to the other electronic components used in the medical equipment. As a result, efforts to reduce the physical size of the medical equipment may be limited by the relatively large size of the inductive couplers. Additionally, electrical noise produced by other electrical components in the medical equipment may be inductively coupled through the windings of the transformer and shock the patient or corrupt the patient's physiological signal. Furthermore, inductive couplers are relatively expensive components that increase the cost of manufacturing the associated piece of medical equipment.

Optical couplers do not experience many of the drawbacks associated with inductive couplers. Optical couplers are typically smaller and less expensive than inductive couplers. Also, optical couplers are not affected by electrical noise present in the medical equipment. For these and other reasons, optical couplers are generally preferred over inductive couplers; however, as discussed below, optical couplers suffer other drawbacks.

A common type of optical coupler uses a light emitting diode (LED) and a photodetector. The LED is connected to the patient leads and the photodetector is connected to the medical equipment. The presence of a patient physiological signal causes the LED to emit a beam of light, which is detected by the photodector and transmitted to the medical equipment as an electric signal. Patient physiological signals may be applied to optical couplers in either analog or digital form. When the physiological signals are applied in analog form, the intensity of the emitted beam of light varies with the amplitude of the analog signal. The photodetector detects the emitted beam of light and produces an electrical signal whose amplitude is proportional to the intensity of the emitted beam of light. Unfortunately, the LEDs do not operate linearly over a broad range of physiological signal amplitudes. As a result, the magnitude of the electric signal transmitted to the medical equipment may not accurately represent the amplitude of the patient physiological signal.

The nonlinearity problem associated with optical couplers may be avoided by converting the analog physiological signal to a digital signal. However, this requires a complex analog-to-digital conversion of the patient physiological signal, which increases the cost and complexity of the associated medical equipment.

As can be readily appreciated from the foregoing discussion, there has developed a need in the medical profession for an apparatus that will permit electrode leads to be optically coupled to medical monitoring and diagnostic equipment while avoiding the nonlinearity and complex analog-to-digital conversion problems associated with optically coupled medical equipment in the prior art. The present invention provides an apparatus for transmitting patient physiological signals that achieves these results.

SUMMARY OF THE INVENTION

In accordance with the present invention, an apparatus for transmitting a patient physiological signal from a first circuit to a second circuit is provided. The apparatus comprises a converter in the first circuit, an optical coupler, and a controller in the second circuit. A physiological signal is applied to the converter. The converter receives a first signal and produces a second signal in response to the first signal such that a time delay from the receipt of the first signal to production of the second signal encodes the patient physiological signal. The controller produces the first signal, receives the second signal, and determines an estimated time delay by measuring the time elapsed between production of the first signal and receipt of the second signal such that the estimated time delay provides a measure of the patient physiological signal. The optical coupler couples the converter to the controller such that the optical coupler transmits the first signal from the controller to the converter and transmits the second signal from the converter to the controller.

In accordance with further aspects of the present invention, the converter comprises a front end circuit, and an echo circuit. The front end circuit receives and conditions the physiological signal and produces a conditioned signal such that a magnitude of the conditioned signal is proportional to the physiological signal. The echo circuit receives the conditioned signal and the first signal and produces the second signal. The first signal comprises a leading edge of a trigger pulse and the second signal comprises a leading edge of an echo pulse.

In accordance with still further aspects of the present invention, the echo circuit comprises a track and ramp circuit and a latch circuit. The track and ramp circuit operates in either a tracking mode or a ramping mode. In the tracking mode, the track and ramp circuit produces a tracking voltage having a magnitude that is related to the magnitude of the conditioned signal. The latch circuit receives the trigger pulse and produces a ramp command voltage in response to a leading edge of an optically transmitted trigger pulse. The ramp command voltage causes the track and ramp circuit to switch to the ramping mode and the magnitude of the tracking voltage changes at a predetermined rate. When the magnitude of the tracking voltage reaches a predetermined level the echo circuit produces the echo pulse.

In accordance with further aspects of the present invention, the controller comprises a clock and a counter. The clock produces clock pulses. The counter begins counting clock pulses when the leading edge of the trigger pulse is produced and stops counting clock pulses when a leading edge of an optically transmitted echo pulse is received. The counter produces an output signal in the form of a count value of clock pulses counted by the counter.

As will be appreciated from the foregoing summary, the invention provides an apparatus for transmitting patient physiological signals to medical equipment through optical couplers.

BRIEF DESCRIPTION OF THE DRAWINGS

The foregoing and other advantages of the present invention will become better understood by reference to the following detailed description when taken in conjunction with the accompanying drawings, wherein.

DETAILED DESCRIPTION OF THE PREFERRED EMBODIMENT

There has developed a need in the medical profession for an apparatus that eliminates the nonlinearity and complex analog-to-digital conversion problems associated with transmitting patient physiological signals through optical couplers to medical equipment. As will become better understood from the following discussion, the present invention is an apparatus that overcomes the problems associated with the prior art.

Figure 1:
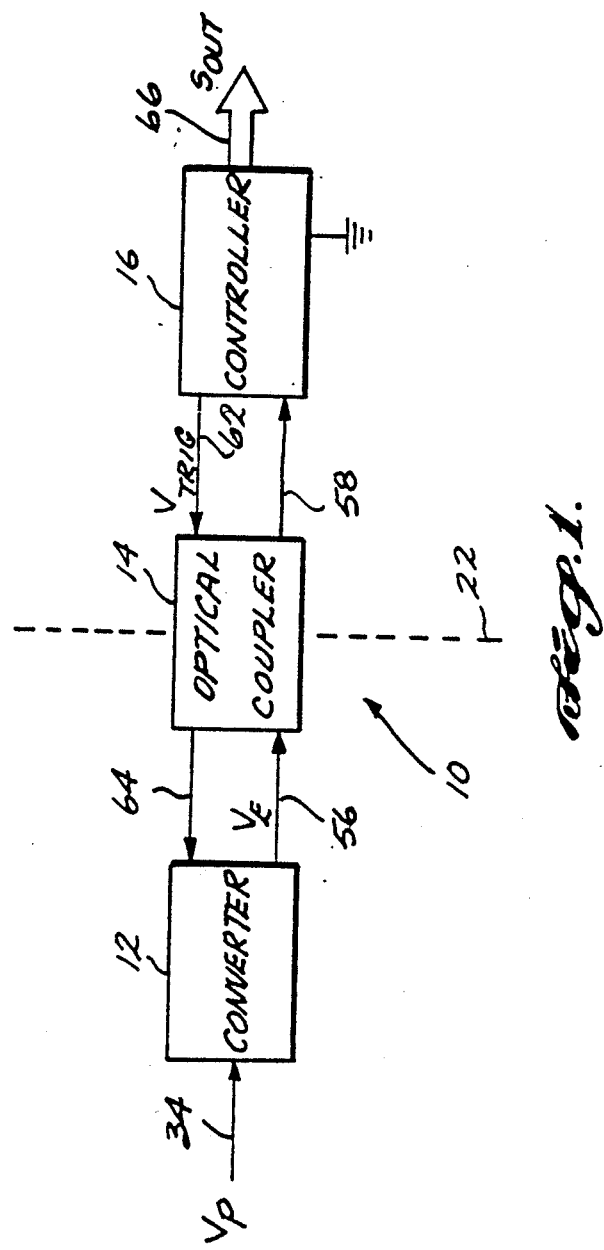
FIG. 1 is a simplified block diagram illustrating broad aspects of a preferred embodiment of the present invention.

Referring initially to FIG. 1, an apparatus 10 is shown that includes a first circuit and a second circuit in accordance with the present invention. The first circuit includes a converter 12 that receives a patient physiological signal, designated $V_P$, via one or more electrode leads 34. The converter 12 is connected to one side of an optical coupler 14 that isolates the converter 12 from ground. The second circuit includes a controller 16 that is connected to the other side of the optical coupler and is grounded. Accordingly, the apparatus 10 includes an isolated first circuit and a nonisolated second circuit. The distinction between the isolated and nonisolated circuits is further illustrated in FIG. 1 by the vertical dashed line 22. It is desirable to encode the $V_P$ signal so that amplitude information contained in the $V_P$ signal may be transmitted through the optical coupler 14 to the controller 16.

The apparatus 10, illustrated in FIG. 1, operates in the manner broadly set forth next. The controller 16 initiates the $V_P$ signal encoding process by producing a trigger signal, designated $V_{TRIG}$, on line 62. The $V_{TRIG}$ signal is produced at some initial time, designated T1. The $V_{TRIG}$ signal may comprise a pulse whose leading edge occurs at time T1. The $V_{TRIG}$ signal is applied to the optical coupler 14, which produces an optically transmitted $V_{TRIG}$ signal on line 64. As will become better understood from the following discussion, the signal on line 64 triggers the converter 12, which causes the converter 12 to produce an echo signal, designated $V_E$, on line 56. The $V_E$ signal is produced at a time, designated T2, that occurs some period of time after the converter receives the optically transmitted $V_{TRIG}$ signal. The $V_E$ signal may also comprise a pulse whose leading edge occurs at time T2. As will be discussed more fully below, a time delay, designated $\Delta T$, from receipt of the optically transmitted $V_{TRIG}$ signal on line 64 and production of the $V_E$ signal encodes the patient physiological signal. For example, the time delay, $\Delta T$, may be proportional to the amplitude of the patient physiological signal, $V_P$.

The $V_E$ signal is applied to the optical coupler 14, which produces an optically transmitted echo signal on line 58. As will become better understood from the following discussion, the controller 16 determines an estimated time delay, designated $\Delta T'$, such that $\Delta T'$ is a measure of the time elapsed between production of the $V_{TRIG}$ signal and receipt of the optically transmitted $V_E$ signal on line 58. Accordingly, $\Delta T'$ provides a measure of the patient physiological signal. The controller produces an output signal, designated $S_{OUT}$, that is a function of $\Delta T'$ and that therefore provides a measure of the patient physiological signal, $V_P$.

Figure 2:
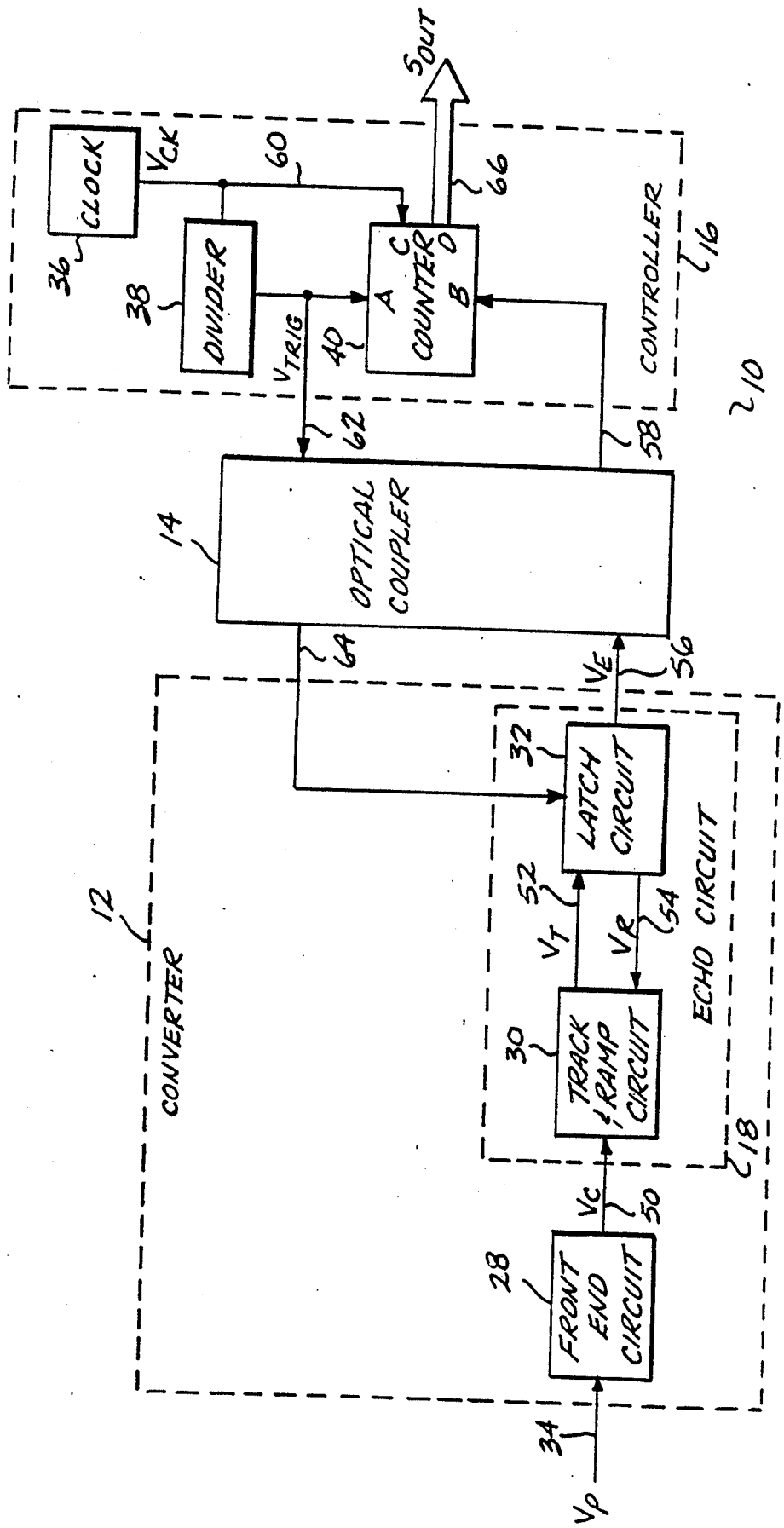
FIG. 2 is a more detailed block diagram of the invention depicted in FIG. 1; and, FIG. 3 is a schematic diagram of an echo circuit suitable for use with the preferred embodiment of the invention depicted in FIG. 2.

FIG. 2 is a block diagram, illustrating in more detail the apparatus 10 depicted in FIG. 1 and discussed above. As illustrated in FIG. 2, the converter 12 comprises front end circuit 28 and echo circuit 18. The echo circuit 18 further comprises a track and ramp circuit 30, and a latch circuit 32. The controller 16 comprises a clock 36, a divider 38, and a counter 40. The counter 40 has two data inputs A and B, a control input C, and an output D.

The apparatus 10 preferably forms a part of medical equipment attached to the patient via one or more patient leads 34. For example, the apparatus 10 may form a part of an ECG monitoring system connected to the patient. In accordance with this example, the front end circuit 28 comprises an ECG preamplifier that receives and appropriately conditions patient ECG signals (i.e., $V_P$). If the ECG monitoring system is a multiple ECG lead system, the ECG preamplifier of the front end circuit 28 may also include lead selection circuitry to permit a desired ECG lead 34 to be selected. Such an ECG preamplifier is well known in the prior art and, hence, is not described in detail herein.

The apparatus 10 illustrated in FIG. 2 operates in the following manner. One or more electrode leads 34 are connected to the front end circuit 28. The patient physiological signal, $V_P$, is applied to the front end circuit 28, which in a conventional manner conditions the $V_P$ signal, and produces a conditioned signal, designated $V_C$, on line 50. For example, if the front end circuit 28 comprises an ECG preamplifier, then the $V_P$ signal may be amplified, DC restored, filtered, and given a DC offset to produce the $V_C$ signal. In any event, the magnitude of the $V_C$ signal is a function of the $V_P$ signal. When the track and ramp circuit 30 receives the $V_C$ signal on line 50, a tracking voltage, designated $V_T$, is produced on line 52. As will become better understood from the following discussion, the magnitude of the $V_T$ signal is related to the $V_C$ signal magnitude. In one preferred embodiment of the present invention, the magnitude of $V_T$ is inversely proportional to the magnitude of the $V_C$ signal.

Turning next to the controller 16, the clock 36 produces clock pulses, designated $V_{CK}$, on line 60. The $V_{CK}$ pulses are applied to the divider 38 and to the data input, C, of the counter 40. The divider 38 divides the frequency of the $V_{CK}$ pulses on line 60 and produces a plurality of $V_{TRIG}$ pulses at a reduced pulse frequency on line 62. The leading edge of a $V_{TRIG}$ pulse on line 62 causes the counter 40 to start counting the $V_{CK}$ pulses on line 60. As discussed above, the optical coupler 14 produces the optically transmitted $V_{TRIG}$ pulse on line 64.

A leading edge of the optically transmitted $V_{TRIG}$ pulse on line 64 causes the latch circuit 32 to produce a ramp command voltage, designated $V_R$, on line 54. As will become better understood from the following discussion, a high $V_R$ voltage on line 54 places the track and ramp circuit 30 in a tracking mode and causes the magnitude of the $V_T$ voltage to track the magnitude of the $V_C$ signal on line 50. Contrariwise, a low $V_R$ voltage on line 54 places the track and ramp circuit 30 in a ramping mode and causes the magnitude of the $V_T$ voltage to change at a predetermined rate. The latch circuit 32 produces the $V_E$ pulse on line 56 when the magnitude of the $V_T$ voltage changes to a predetermined level. In one preferred embodiment, the $V_T$ voltage decays at a constant rate and the $V_E$ pulse is produced on line 56 when the magnitude of $V_T$ decays to zero volts. As will be discussed more fully below, the latch circuit 32 is set when the pulse on line 64 is applied to OA3, and the latch circuit 32 is reset when the $V_T$ voltage changes to the predetermined level.

As noted above, the optical coupler 14 produces the optically transmitted $V_E$ pulse on line 58. A leading edge of the pulse on line 58 causes the counter 40 to stop counting the $V_{CK}$ pulses. The counter 40 produces the $S_{OUT}$ signal on output bus 66. The $S_{OUT}$ signal has a value equal to the number of $V_{CK}$ pulses counted by the counter 40 during the elapsed time between the production of the $V_{TRIG}$ pulse on line 60 and receipt of the optically transmitted $V_E$ pulse on line 58 (i.e., $\Delta T$). Thus, as discussed above, the value of the $S_{OUT}$ signal is proportional to the magnitude of the $V_C$ signal and, hence, proportional to the amplitude of the patient physiological signal, $V_P$.

Alternatively, the counter 40 may be a free running counter that continuously counts the $V_{CK}$ pulses produced by the clock 36. In this alternative embodiment, a count value of the $V_{CK}$ pulses counted by the counter 40 at a time corresponding to the time the leading edge of the $V_{TRIG}$ pulse is produced on line 62, is loaded into a first, or start, register. A subsequent count value of the $V_{CK}$ pulses counted by the counter 40 at a time corresponding to the time the leading edge of the pulse on line 58 is produced, is loaded into a second, or stop, register. The difference between the count values in the start and stop registers is the number of $V_{CK}$ pulses counted by the free running counter 40 between production of the $V_{TRIG}$ pulse on line 62 and receipt of the $V_E$ pulse on line 58. Accordingly, the $S_{OUT}$ signal has a value equal to the difference in count values.

Figure 3:
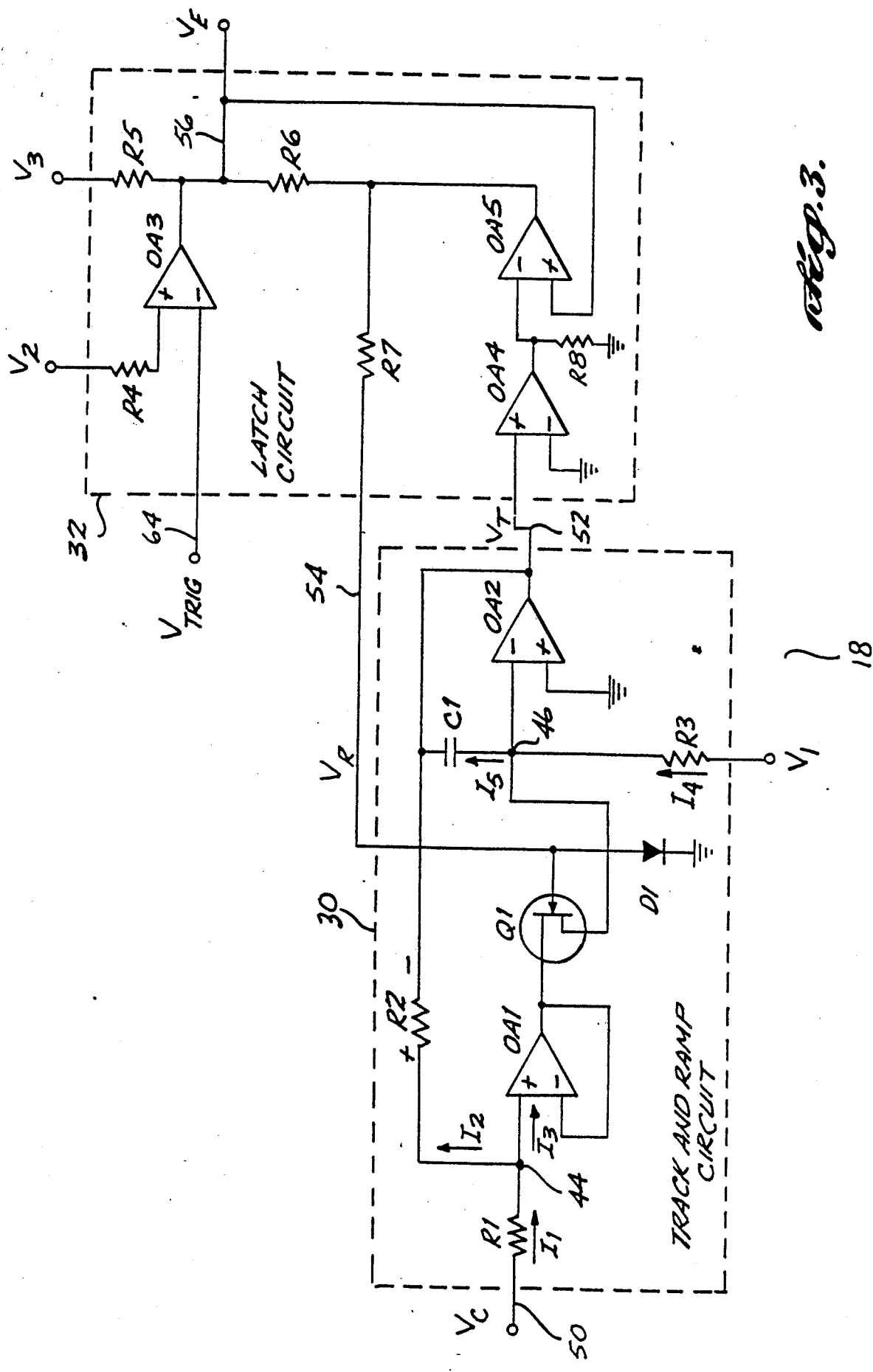

FIG. 3 is a simplified schematic diagram of the echo circuit 18 depicted in FIG. 2 and discussed above. The track and ramp circuit 30 comprises two high impedance operational amplifiers, designated OA1 and OA2; a FET transistor, designated Q1; a diode, designated D1; three resistors, designated R1, R2, and R3; and one capacitor, designated C1. For reasons that will become better understood from the following discussion, the values of R1 and R2 are equal and R3 is a high-precision resistor. The latch circuit 32 comprises three operational amplifiers connected as comparators, designated OA3, OA4, and OA5, and five resistors, designated R4, R5, R6, R7, and R8.

The conditioned signal, $V_C$, such as a conditioned ECG signal, for example, is applied to one end of R1 via line 50. The other end of R1 is connected to one end of R2 and to the noninverting input of OA1. The common connection between R1, R2 and the noninverting input of OA1 forms a node 44. The output of OA1 is connected to the inverting input of OA1 and to the drain of Q1. The source of Q1 is connected to one side of C1, to the inverting input of OA2, and to one side of R3. The common connection between C1, the source of Q1, and the inverting input of OA2 forms a node 46. The other side of R3 is connected to a positive voltage source, designated $V_1$. The gate of Q1 is connected to one end of R7 and to the anode of D1. The cathode of D1 is connected to ground. The other end of R2 is connected to the other end of C1, to the output of OA2, and to the noninverting input of OA4. The noninverting input of OA2 and the inverting input of OA4 are connected to ground. The output of OA4 is connected to the inverting input of OA5 and to ground through R8. The optically transmitted $V_{TRIG}$ pulse is applied to the inverting input of OA3 via line 64. A positive voltage source, designated $V_2$ is applied to one end of R4. The other end of R4 is connected to the noninverting input of OA3. The output of OA3 is connected to one end of R5, to the other end of R6, and to the noninverting input of OA5. The other end of R6 is connected to the other end of R7 and to the output of OA5. The other end of R5 is connected to a positive voltage source, designated $V_3$. The $V_T$ voltage is formed at the OA2 output on line 52, the $V_R$ voltage is formed at the gate of Q1 on line 54, and the $V_E$ pulse is formed at the output of OA3 on line 56.

The operation of the echo circuit 18 illustrated in FIG. 3 and described above is discussed next. As noted above, the track and ramp circuit 30 operates in one of two modes: a tracking mode or a ramping mode. The particular operating mode of the track and ramp circuit 30 is determined by the state of Q1. As will be discussed more fully below, the track and ramp circuit 30 operates in the tracking mode when Q1 is closed and operates in the ramping mode when Q1 is open. The state of Q1 (viz, open or closed) is controlled by the $V_R$ voltage on line 54.

The operation of the track and ramp circuit 30 during the tracking mode is discussed first. Initially, a pulse is absent from line 64, thereby causing the input of OA3 to be made high by the $V_2$ voltage. The high input of OA3 causes OA3 to provide a high impedance, which, in turn, causes the output of OA3 to be pulled high by $V_3$ and $R_5$. A high OA3 output forces the ramp command voltage, $V_R$, to go high. A high $V_R$ voltage on line 54 turns on Q1, which, as noted above, places the track and ramp circuit 30 in the tracking mode. When Q1 is closed (i.e., on), the output of OA1 is connected to the inverting input of OA2. Since the noninverting input of OA2 is grounded, the inverting input of OA2, the output of OA1 and both inputs of OA1 are also grounded. Accordingly, the node 44 is also grounded.

A current, designated $I_1$, is produced by $V_C$ and R1 and flows into the node 44. Another current, designated $I_2$, flows out of the node 44 through R2 and a third current, designated $I_3$, flows out of the node 44 into the noninverting input of OA1. Since, as noted above, OA1 is a high impedance operational amplifier, there is essentially no current flow into the noninverting input of OA2 (i.e., $I_3=0$). Since the current flow into the node 44 must equal the current flow out of the node 44 (i.e., $I_1=I_2+I_3$) and since $I_3$ substantially equals zero, $I_1$ is substantially equal to $I_2$. As noted above, the values of R1 and R2 are equal. Accordingly, the magnitude of the voltage produced by $I_2$ and R2 is equal to the inverse of the magnitude of the voltage produced by $I_1$ and R1. The voltage produced by $I_2$ and R2 is formed at the output of OA2 and, hence, forms the tracking voltage, $V_T$, on line 52. Thus, during the tracking mode the magnitude of the tracking voltage is equal to the inverse of the conditioned physiological signal amplitude (i.e., $V_T = -V_C$). In a particular working model formed in accordance with the preferred embodiment of the invention, the value of the $V_C$ signal magnitude is negative and, hence, the value of the $V_T$ voltage magnitude is positive. The positive $V_T$ voltage allows the output of OA4 to be grounded through R8. The grounded output of OA4 and the high output of OA3 cause the output of OA5 to be high, which allows $V_R$ to remain high and retain the reset state of latch circuit 32.

The ramping mode of the track and ramp circuit 30 is discussed next. When the leading edge of the pulse on line 64 is applied to the inverting input of OA3, OA3 switches states and the output of OA3 goes low. A low OA3 output forces the $V_R$ voltage to go low. A low $V_R$ voltage on line 54 causes Q1 to turn off (i.e., open), which places the track and ramp circuit 30 in the ramping mode. The low OA3 output also causes OA5 to switch states and produce a low output. The low OA5 output sets the latch circuit such that the $V_R$ voltage is latched to a low value. As a result, the $V_R$ voltage remains low after the pulse on line 64 is removed. When Q1 opens, the output of OA1 is disconnected from the inverting input of OA2. A constant current, designated $I_4$, is a precision current and is produced by $V_1$ and R3 and flows into the node 46. Since, as noted above, Q1 is open and OA2 is a high impedance operational amplifier, the current flowing into the node 46 substantially equals a current, designated $I_5$, flowing out of the node 46 through C1 (i.e., $I_4=I_5$). As is well known in the electrical art, a constant current flow through a capacitor produces a constant rate of change in the capacitor voltage. Since $I_4$ is a constant current, $I_5$ is also a constant current. Accordingly, the flow of $I_5$ through C1 causes the voltage across C1, i.e., the tracking voltage $V_T$, to change at a constant rate. In accordance with one preferred embodiment of the invention, the direction of $I_5$ causes the $V_T$ voltage to decay at a constant rate.

When the $V_T$ voltage on line 52 decays to zero volts, the latch circuit 32 resets. More specifically, when $V_T$ decays to zero, OA4 switches states and the output of OA4 goes low. The low output of OA4 causes OA5 to switch states and produce a high output. The high output of OA5 forces $V_E$ to go high, thereby producing the leading edge of a $V_E$ pulse on line 56. As noted above and illustrated in FIGS. 1 and 2, the $V_E$ pulse is applied to the optical coupler 14 via line 56, which produces the optically transmitted $V_E$ pulse on line 58. The high output of OA5 also causes the $V_R$ voltage on line 54 to go high, which turns on Q1 and returns the echo circuit 18 to the tracking mode.

As can be readily appreciated from the foregoing description, the present invention provides an apparatus for transmitting a patient physiological signal from an isolated circuit to a nonisolated circuit through an optical coupler. While a preferred embodiment of the invention has been illustrated and described herein, it is to be understood that, within the scope of the appended claims, various changes could be made. For example, the invention can be used with medical monitoring and diagnostic equipment other than an ECG monitor system. Furthermore, while the echo circuit has been illustrated and described in terms of discrete components, it could also be fabricated as an integrated circuit. Hence the invention can be practiced otherwise than is specifically described herein.

The embodiments of the invention in which an exclusive property or privilege is claimed are defined as follows:

1. An apparatus for transmitting a patient physiological signal, the apparatus comprising:
    (a) a converter including means for receiving a first signal and the patient physiological signal and for producing a second signal in response thereto, such that a time delay from receipt of said first signal to production of said second signal encodes said patient physiological signal;
    (b) control means comprising means for producing said first signal, means for receiving said second signal, and means for determining an estimated time delay by measuring the time elapsed between the production of said first signal and receipt of said second signal, whereby the estimated time delay provides a measure of the patient physiological signal; and,
    (c) optical coupler means coupled to the converter and to the control means such that said optical coupler means transmits said first signal from said control means to said converter and transmits said second signal from said converter to said control means.

2. The apparatus of claim 1, wherein said converter comprises:
    (a) front end circuit means coupled to receive said patient physiological signal, said front end circuit means conditioning said patient physiological signal and producing a conditioned signal, such that a magnitude of said conditioned signal is a function of said patient physiological signal; and,
    (b) echo circuit means coupled to said front end circuit means for receiving said conditioned signal, said echo circuit means receiving said first signal and producing said second signal, wherein said first signal comprises a leading edge of a trigger pulse and said second signal comprises a leading edge of an echo pulse.

3. The apparatus of claim 2, wherein said echo circuit means comprises:

(a) track and ramp circuit means coupled to receive said conditioned signal and produce a tracking voltage, such that when said track and ramp circuit means is in a tracking mode a magnitude of said tracking voltage is related to said magnitude of said conditioned signal and when said track and ramp circuit means is in a ramping mode said magnitude of said tracking voltage changes at a predetermined rate; and, (b) latch circuit means coupled to said track and ramp circuit means, said latch circuit means receiving said trigger pulse and producing a ramp command voltage in response to said leading edge of said trigger pulse and removing said ramp command voltage when said tracking voltage changes to said predetermined level, such that a magnitude of said ramp command voltage determines whether said track and ramp circuit means is in said tracking mode or said ramping mode.

4. The apparatus claimed in claim 3, wherein said magnitude of said tracking voltage is inversely proportional to said conditioned signal.

5. The apparatus of claim 3, wherein said track and ramp circuit means is in said tracking mode when said magnitude of said ramp command voltage has a high value and in said ramping mode when said magnitude of said ramp command voltage has a low value.

6. The apparatus of claim 5, wherein said magnitude of said ramp command voltage has a high value when said latch circuit means is reset and a low value when said latch circuit means is set.

7. The apparatus of claim 3, wherein said magnitude of said tracking voltage changes at a constant rate when said track and ramp circuit means is in said ramping mode.

8. The apparatus of claim 7, wherein said track and ramp circuit means is in said tracking mode when said magnitude of said ramp command voltage has a high value and in said ramping mode when said magnitude of said ramp command voltage has a low value.

9. The apparatus of claim 8, wherein said magnitude of said ramp command voltage has a high value when said latch circuit means is reset and a low value when said latch circuit means is set.

10. The apparatus of claim 3, wherein said magnitude of said tracking voltage decays at a constant rate when said track and ramp circuit means is in said ramping mode.

11. The apparatus of claim 10, wherein said track and ramp circuit means is in said tracking mode when said magnitude of said ramp command voltage has a high value and in said ramping mode when said magnitude of said ramp command voltage has a low value.

12. The apparatus of claim 11, wherein said magnitude of said ramping voltage has a high value when said latch circuit means is reset and a low value when said latch circuit means is set.

13. The apparatus of claim 12, wherein said latch circuit means produces said echo pulse and resets when said magnitude of said tracking voltage decays to zero volts.

14. The apparatus of claim 2, wherein said means for determining an estimated time delay comprises:
(a) a clock for producing clock pulses at a clock pulse frequency;
(b) a divider coupled to said clock for dividing said clock pulse frequency and producing said trigger pulse; and,
(c) counter means coupled to said clock and said divider for receiving said clock pulses and said trigger pulse, wherein said counter means starts counting said clock pulses when said counter means receives said leading edge of said trigger pulse and stops counting when said counter means receives said leading edge of said echo pulse, said counter means producing an output signal in the form of clock pulses counted by said counter means.

15. The apparatus of claim 14, wherein said echo circuit means comprises:
(a) track and ramp circuit means coupled to receive said conditioned signal and produce a tracking voltage, such that when said track and ramp circuit means is in a tracking mode a magnitude of said tracking voltage is related to said magnitude of said conditioned signal and when said track and ramp circuit means is in a ramping mode said magnitude of said tracking voltage changes at a predetermined rate; and,
(b) latch circuit means coupled to said track and ramp circuit means, said latch circuit means receiving said trigger pulse and producing a ramp command voltage in response to said leading edge of said trigger pulse and removing said ramp command voltage when said tracking voltage changes to said predetermined level, such that a magnitude of said ramp command voltage determines whether said track and ramp circuit means is in said tracking mode or said ramping mode.

16. The apparatus claimed in claim 15, wherein said magnitude of said tracking voltage is inversely proportional to said conditioned signal.

17. The apparatus of claim 15, wherein said track and ramp circuit means is in said tracking mode when said magnitude of said ramp command voltage has a high value and in said ramping mode when said magnitude of said ramp command voltage has a low value.

18. The apparatus of claim 17, wherein said magnitude of said ramp command voltage has a high value when said latch circuit means is reset and a low value when said latch circuit means is set.

19. The apparatus of claim 18, wherein said magnitude of said tracking voltage decays at a constant rate and said latch circuit means produces said echo pulse and resets when said magnitude of said tracking voltage decays to zero volts.

20. The apparatus of claim 2, wherein said front end circuit means comprises an ECG preamplifier.

21. The apparatus of claim 20, wherein said means for determining an estimated time delay comprises;
(a) a clock for producing clock pulses at a clock pulse frequency;
(b) a divider coupled to said clock for dividing said clock pulse frequency and producing said trigger pulse; and,
(c) counter means coupled to said clock and said divider for receiving said clock pulses and said trigger pulse, wherein said counter means starts counting said clock pulses when said counter means receives said leading edge of said trigger pulse and stops counting when said counter means receives said leading edge of said echo pulse, said counter means producing an output signal in the form of clock pulses counted by said counter means.

22. The apparatus of claim 21, wherein said echo circuit means comprises:
(a) track and ramp circuit means coupled to receive said conditioned signal and produce a tracking voltage, such that when said track and ramp circuit means is in a tracking mode a magnitude of said tracking voltage is related to said magnitude of said conditioned signal and when said track and ramp circuit means is in a ramping mode said magnitude of said tracking voltage changes at a predetermined rate; and,
(b) latch circuit means coupled to said track and ramp circuit means, said latch circuit means receiving said trigger pulse and producing a ramp command voltage in response to said leading edge of said trigger pulse and removing said ramp command voltage when said tracking voltage attains a predetermined level, such that a magnitude of said ramp command voltage determines whether said track and ramp circuit means is in said tracking mode or said ramping mode.

23. The apparatus claimed in claim 22, wherein said magnitude of said tracking voltage is inversely proportional to said conditioned signal.

24. The apparatus of claim 22, wherein said track and ramp circuit means is in said tracking mode when said magnitude of said ramp command voltage has a high value and in said ramping mode when said magnitude of said ramp command voltage has a low value.

25. The apparatus of claim 24, wherein said magnitude of said ramp command voltage has a high value when said latch circuit means is reset and a low value when said latch circuit means is set.

26. The apparatus of claim 25, wherein said magnitude of said tracking voltage decays at a constant rate and said latch circuit means produces said echo pulse and resets when said magnitude of said tracking voltage decays to zero volts.

* * * * *